United States Patent
Engl et al.

(10) Patent No.: US 9,423,382 B2
(45) Date of Patent: Aug. 23, 2016

(54) TEST HEAD FOR TESTING A WORKPIECE HAVING AN ULTRASONIC TRANSDUCER CONFIGURATION CONTAINING A PLURALITY OF ULTRASONIC TRANSDUCERS AND PROCESS FOR PRODUCING SUCH A TEST HEAD

(71) Applicants: INTELLIGENDT SYSTEMS & SERVICES GMBH, Erlangen (DE); FRAUNHOFER GESELLSCHAFT ZUR FOERDERUNG DER ANGEWANDTEN FORSCHUNG E.V., Munich (DE)

(72) Inventors: Guenter Engl, Erlangen (DE); Michael Kroening, Saarbruecken (DE); Henning Heuer, Dresden (DE); Thomas Herzog, Dresden (DE)

(73) Assignees: Areva GmbH, Erlangen (DE); Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 415 days.

(21) Appl. No.: 14/016,423

(22) Filed: Sep. 3, 2013

(65) Prior Publication Data
US 2014/0000371 A1 Jan. 2, 2014

Related U.S. Application Data

(63) Continuation of application No. PCT/EP2012/053262, filed on Feb. 27, 2012.

(30) Foreign Application Priority Data

Mar. 3, 2011 (DE) .......................... 10 2011 005 063
Feb. 6, 2012 (DE) .......................... 10 2012 201 715

(51) Int. Cl.
*G01N 29/34* (2006.01)
*G01N 29/24* (2006.01)
(Continued)

(52) U.S. Cl.
CPC .............. *G01N 29/34* (2013.01); *B06B 1/0633* (2013.01); *G01N 29/2437* (2013.01); *G01N 29/28* (2013.01); *G10K 11/004* (2013.01); *G01N 2291/106* (2013.01); *G01N 2291/2638* (2013.01)

(58) Field of Classification Search
CPC ... G01N 29/2437; G01N 29/28; G01N 29/34; G01N 2291/106; G01N 2291/2638; B06B 1/0633; G10K 11/004
USPC .......................................................... 73/640
See application file for complete search history.

(56) References Cited

U.S. PATENT DOCUMENTS 5,050,703 A * 9/1991 Graff ................. G01N 29/2412
181/106
5,744,898 A * 4/1998 Smith ..................... B06B 1/064
310/334

(Continued)

FOREIGN PATENT DOCUMENTS

DE 10018355 * 12/2001 ................ B06B 1/06
EP 1145772 A2 10/2001
GB WO2005107962 * 11/2005 ................ B06B 1/06

OTHER PUBLICATIONS

International Search Report of PCT/EP2012/053262, Dated June 25, 2012.

*Primary Examiner* — J M Saint Surin
(74) *Attorney, Agent, or Firm* — Laurence A. Greenberg; Werner H. Stemer; Ralph E. Locher

(57) ABSTRACT

A test head for testing a workpiece has an ultrasonic transducer configuration with a plurality of ultrasonic transducers. The test head further contains a carrier matched to a surface contour of the workpiece, a damping layer arranged on the carrier, and a flexible conductor foil configuration, which is arranged on the damping layer and has a number of electrically separated conductor tracks which corresponds to the number of transducer elements. The transducer elements are arranged on the conductor tracks alongside one another in at least one row, and in each case are electrically contact-connected to one of the conductor tracks.

14 Claims, 4 Drawing Sheets

(51) Int. Cl.
  *G01N 29/28* (2006.01)
  *G10K 11/00* (2006.01)
  *B06B 1/06* (2006.01)

(56) References Cited

U.S. PATENT DOCUMENTS

| | | |
|---|---|---|
| 5,792,058 A | 8/1998 | Lee et al. |
| 6,508,133 B1 * | 1/2003 | Adachi .................. G01F 1/662 |
| | | 310/334 |
| 2003/0173870 A1 * | 9/2003 | Simon Hsu ........... B06B 1/0622 |
| | | 310/334 |
| 2004/0011134 A1 * | 1/2004 | Sato ........................ B06B 1/064 |
| | | 73/632 |
| 2004/0100163 A1 * | 5/2004 | Baumgartner ........ B06B 1/0622 |
| | | 310/334 |
| 2005/0039323 A1 * | 2/2005 | Sheljaskow ............ G10K 11/02 |
| | | 29/594 |
| 2006/0103265 A1 | 5/2006 | Miyoshi |

* cited by examiner

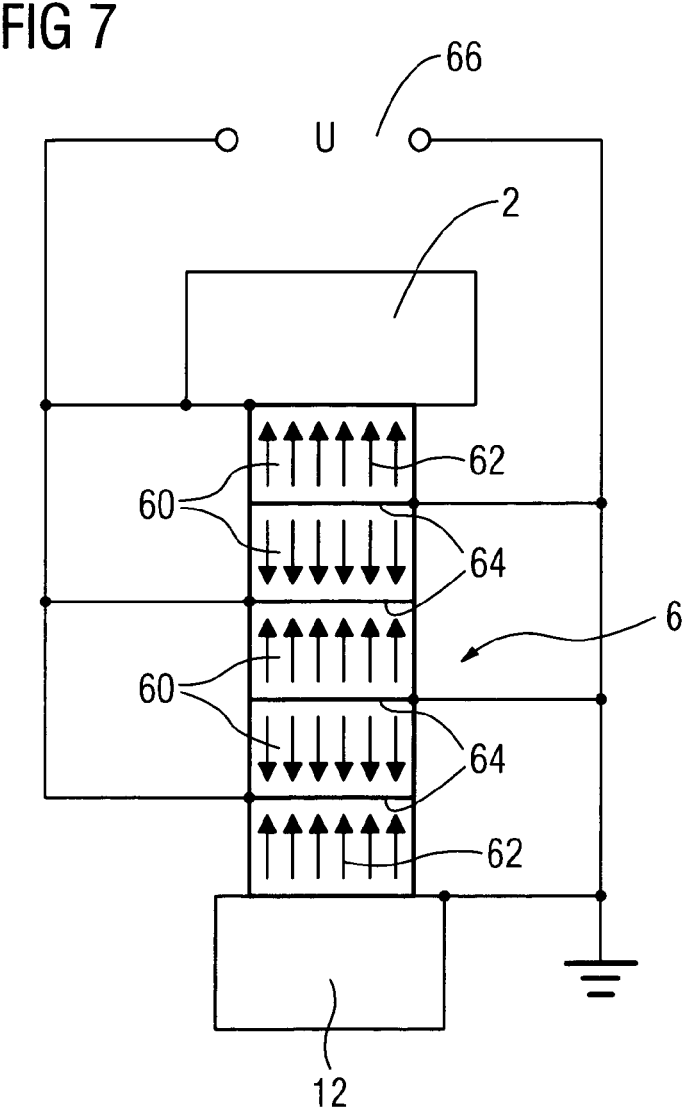

TEST HEAD FOR TESTING A WORKPIECE HAVING AN ULTRASONIC TRANSDUCER CONFIGURATION CONTAINING A PLURALITY OF ULTRASONIC TRANSDUCERS AND PROCESS FOR PRODUCING SUCH A TEST HEAD

CROSS-REFERENCE TO RELATED APPLICATION

This is a continuation application, under 35 U.S.C. §120, of copending international application No. PCT/EP2012/053262, filed Feb. 27, 2012, which designated the United States; this application also claims the priority, under 35 U.S.C. §119, of German patent applications DE 10 2011 005 063.9, filed Mar. 3, 2011 and DE 10 2012 201 715.1, filed Feb. 6, 2012; the prior applications are herewith incorporated by reference in their entireties.

BACKGROUND OF THE INVENTION

Field of the Invention

The invention relates to an ultrasonic sensor unit for testing a workpiece having an ultrasonic transducer configuration containing a plurality of ultrasonic transducers. In addition, the invention relates to a process for producing such a test head.

For the non-destructive testing of materials with ultrasound, which are known as phased-array sensor units are used in a large number of applications, which contain a multiplicity of ultrasonic transducer elements arranged beside one another in a linear or matrix form, and with which, under phase control, the angle of incidence and the areas of the depth of focus of the ultrasonic signal transmitted into the workpiece as well as the depth of focus in the receiving mode can be varied. Sensor units of this type are also designated phased-array sensor units. Most frequently, sensor units having a linear configuration of the ultrasonic transducers, which are known as line arrays, are used. For analytical interpretations, the echo signals (A scans) received at various angles of incidence can be combined into a sector image (sector scan), by which a cross-sectional image—known as B-scan image—of the test volume with a representation of the reflectors contained therein is obtained. As a rule, a minimum of at least 12 ultrasonic transducers are needed for a linear array in order to permit a good reconstruction.

The sector image of a linear array supplies two-dimensional images which, combined, result in a three-dimensional image. In the third dimension, perpendicular to the sector image plain, however, only restricted contrast and resolution sensitivity are obtained. Thus, for example, flat defects with oblique orientation towards the sector image plain cannot be found.

Therefore, for a three-dimensional reconstructed image, a two-dimensional configuration of ultrasonic transducers is needed, known as a matrix array. In the case of a matrix array, at least 12 linear arrays each having 12 ultrasonic transducers, i.e. 12×12 or 144 ultrasonic transducers, are accordingly necessary, which have to be arranged close together. According to the scanning theorem, the dimensions of the ultrasonic transducers must correspond in each direction to half a wavelength of the ultrasonic signal used for testing. For the testing of a workpiece formed of steel with a testing frequency of 3 MHz, the active area of each single ultrasonic transducer would accordingly amount to about 1×1 mm². Accordingly, the sensor unit would have a small aperture of 12×12 mm².

With such a small aperture, however, synthetic focusing at relatively large component depths is not possible, for which reason linear arrays having substantially higher numbers of elements, for example 64 elements, are generally used, so that a corresponding matrix array would contain 64×64 ultrasonic transducers. Matrix arrays having such a high number of ultrasonic transducers are, however, impractical in view of the multiplicity of ultrasonic channels needed and the problems associated with the cabling and wiring.

Instead of the use of such phased arrays, it is known, for example from Engl, G., Kröning, M., Reddy, K., Schreiber, J.: entitled "NDT and its Value for Structural Safety", 2010 Proceedings International Scientific Conference "Optical Techniques and Nanotools for Material and Life Sciences" (ONT4MLS-2010), June 2010, Minsk, Belarus, to use what are known as thinned linear arrays or matrix arrays which violate the scanning theorem and are designated migration arrays or sampling phased arrays. In the case of such a migration array, the ultrasonic transducers are activated individually one after another. The echo signals generated in the workpiece are received by all the ultrasonic transducers and a two-dimensional or three-dimensional ultrasonic image is reconstructed from the echo signals received. Since the ultrasonic transducers are not activated simultaneously with a phase shift in relation to one another in order to generate a sound beam in a specific direction of incidence, the electronics for phase control can be dispensed with. In this way, it is possible to build up matrix arrays with which it is possible, by using a practicable number of ultrasonic transducers, to achieve a size of the aperture that is practical in terms of performance of the test. However, known migration arrays having a relatively large aperture can be used only on flat surfaces.

In order to be able to test workpieces having curved surfaces using contact technology, the test head must be matched to the contour, since a gap between the transmitting and receiving surface (sensor unit sole) and the surface of the workpiece must generally not exceed half the wavelength of the ultrasound wave used. Since the piezoelectric material for the usual technical frequencies consists of rigid ceramic, piezoelectric composites can themselves be bent only to a limited extent. In addition, the bending increases the risk of subsequent separations and cracking, which would make the sensor unit unusable.

A further possibility is the fitting of a delay wedge matched to the surface contour of the workpiece, for example formed of PMMA. However, as a result of the different propagation paths of the ultrasound in the delay wedge, the reconstruction of the ultrasonic image on the basis of the aforementioned migration technology can be made considerably more difficult, for example as a result of focusing or defocusing caused by the delay wedge and also of echo signals from the delay wedge/workpiece interface. Frequently, for example when testing boreholes, such a solution is already not possible for geometric reasons. This is similarly also true when using liquid i.e. immersion delay lines. All the possibilities mentioned become increasingly more problematic in their application if the group aperture is expanded by thinning of the transducer element array.

SUMMARY OF THE INVENTION

The invention is therefore based on the object of specifying a sensor unit for testing a workpiece having an ultrasonic transducer configuration containing a plurality of ultrasonic transducer elements which, with a large aperture matched to the surface contour of the workpiece, can be produced simply in fabrication terms. In addition, the invention is based on the object of specifying a process for producing such a test head.

With the foregoing and other objects in view and, in accordance with the invention, a test head is specified. Accordingly, the test head contains an ultrasonic transducer configuration with a plurality of ultrasonic transducer elements and further contains a carrier which is matched to the surface contour of the workpiece and on which a damping layer is arranged. Arranged on the damping layer is a flexible conductor foil configuration having a number of electrically separated conductor tracks corresponding to the number of ultrasonic transducers, on which the ultrasonic transducers are arranged beside one another in at least one row and electrical contact is respectively made with one of the conductor tracks.

As a result of this measure, it is possible to provide a test head with a large aperture even for workpieces with a curved surface contour.

The second-named object is achieved, according to the invention, by a process, according to which, by using electrically mutually separated conductor tracks of a conductor foil configuration, contact is made with a plurality of ultrasonic transducers corresponding to the number of conductor tracks. Then, on the reverse side of the conductor foil, facing away from the ultrasonic transducers, a damping layer is applied which is flexible, at least during a processing time, or the conductor foil populated with the ultrasonic transducers is applied to a pre-formed damping layer which is likewise flexible, at least during the processing time. The conductor foil configuration provided with the ultrasonic transducers and the damping layer in this way is then applied to a carrier matched to a surface contour of a workpiece to be tested.

Other features which are considered as characteristic for the invention are set forth in the appended claims.

Although the invention is illustrated and described herein as embodied in test head for testing a workpiece having an ultrasonic transducer configuration containing a plurality of ultrasonic transducer elements and a process for producing such a test head, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 7 is a circuit diagram of a particularly suitable ultrasonic transducer, built up from a piezoelectric stack, in a basic image.

DETAILED DESCRIPTION OF THE INVENTION

Figure 1:
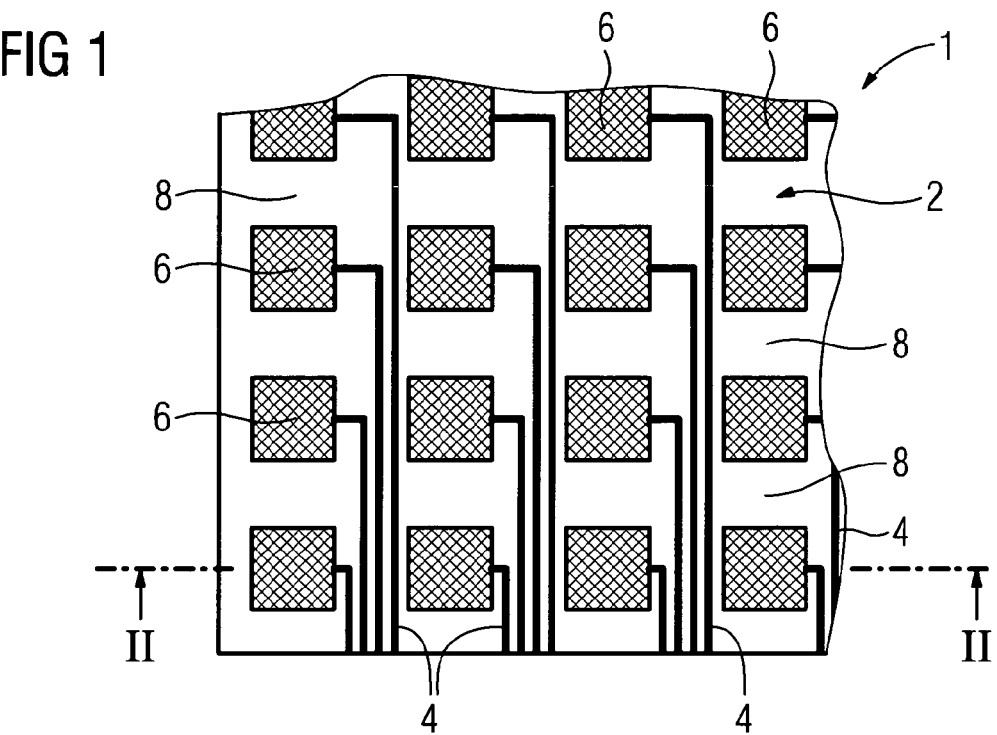
FIG. 1 is a diagrammatic, plan view of a conductor foil configuration according to the invention populated with a matrix-like configuration of ultrasonic transducer elements.

Referring now to the figures of the drawings in detail and first, particularly to FIG. 1 thereof, as a starting product for the production of a test head according to the invention, a flexible conductor foil configuration 1 is shown having a plurality of electrically mutually insulated conductor tracks 4. The conductor foil configuration 1 has a plurality of ultrasonic transducer elements 6 soldered or adhesively bonded with an electrically conductive adhesive, electrical contact being made between each ultrasonic transducer 6 and a respective conductor track 4. In this way, the ultrasonic transducer configuration is formed which contains a plurality of the ultrasonic transducer elements 6.

The electrically mutually separated conductor tracks 4 can either be arranged on a flat side of a conductor foil 2 on which the ultrasonic transducer elements 6 are located. As an alternative to this, the conductor tracks 4 can also be found on the opposite underside of the conductor foil configuration 1 and each be provided via through-contacts with surface connecting structures matched to the dimension of the ultrasonic transducer elements 6.

Accordingly, the ultrasonic transducer elements 6 can be activated independently of one another, so that the ultrasonic transducer elements 6 can transmit individual ultrasonic signals and the ultrasonic signals received by the ultrasonic transducer elements 6 can be processed independently of one another. In the example illustrated, the conductor foil configuration 1 is formed by a coherent, one-piece conductor foil 2. In principle, however, it is also possible, for example, to use separate conductor foils for each row.

The ultrasonic transducer elements 6 are separated from one another by interspaces 8, so that, by using a reduced number of ultrasonic transducer elements 6, it is possible to provide either a test head extended in one longitudinal direction and having a linear transducer element array (linear ultrasonic transducer element configuration), in which the ultrasonic transducer elements 6 are arranged beside one another in a single row, or a large-area test head having a matrix-like transducer element array (matrix-like ultrasonic transducer element configuration), in which the ultrasonic transducer elements 6 are arranged in a plurality of rows beside one another.

Figure 2:
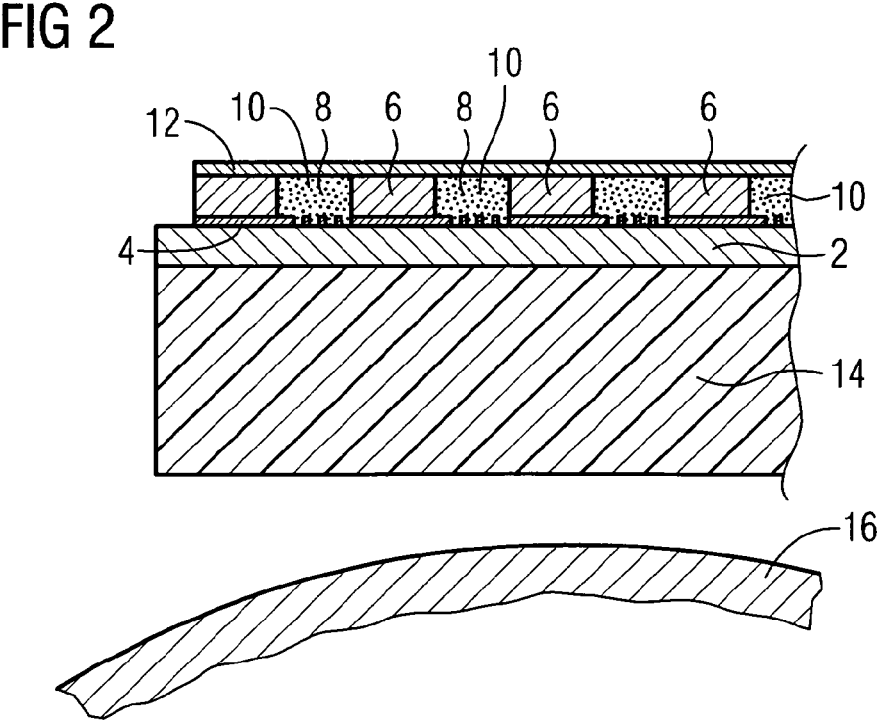
FIG. 2 is a partial sectional view of the conductor foil configuration populated with the ultrasonic transducer elements supplemented by a grounding foil arranged over the ultrasonic transducers.

The sectional image of FIG. 2 shows a section of an intermediate product for the production of the test head according to the invention, in which the interspaces 8 are filled with an absorber material 10. For this purpose, the interspaces 8 are potted with an epoxy resin or with a permanently elastic material, for example. In order to protect the contact areas of the ultrasonic transducer elements 6 that face away from the conductor foil 2, before the potting with epoxy resin or with a permanently elastic material, self-adhesive protective films, which can be detached after the potting, are applied to the contact surfaces.

The ultrasonic transducer elements 6 are additionally covered by a coherent grounding foil 12. The preferably $\lambda/4$ thick grounding foil 12 can also be applied before the absorber material 10 is introduced or poured in. In this case, separate protection of the contact areas is no longer necessary. Prior application of the grounding foil 12 is therefore also advantageous, since the foil can be provided with solder, which can additionally also have a high melting point, over the entire area. In the case of subsequent application of the grounding foil 12, the soldering must either be carried out with low-melting-point solder or the contact must be made with a conductive adhesive.

Applied to the reverse side of the conductor foil 2 is a damping layer 14 which is likewise elastic, at least during a processing time needed until the application of the intermediate product containing the damping layer 14 and the conductor foil 2 populated with the ultrasonic transducer elements 6 to a curved carrier 16 indicated schematically in FIG. 2.

Figure 3:
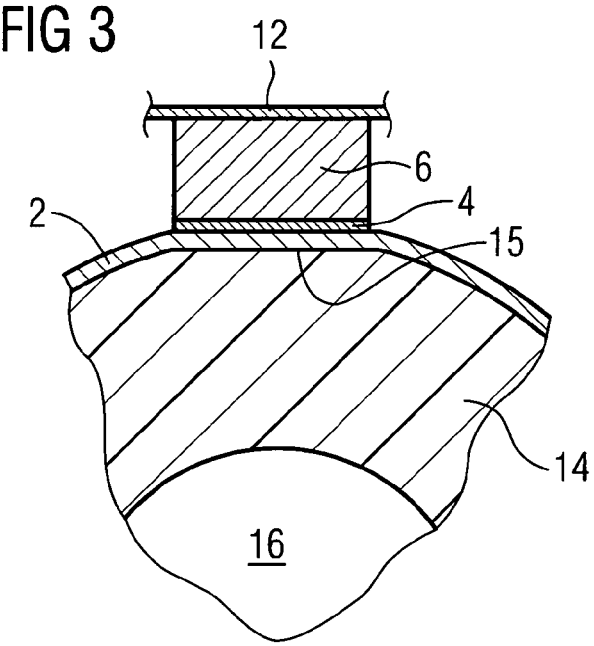
FIG. 3 is a sectional view of a detail containing only one ultrasonic transducer element from the populated conductor foil configuration applied to a prefabricated damping layer.

The damping layer 14 can either be applied to the reverse side of the conductor foil 2 as a layer or, alternatively, be prefabricated in accordance with FIG. 3, onto which damping layer the conductor foil 2 is then adhesively bonded before or after the conductor is populated with the ultrasonic transducer elements 6. The last-named procedure has the advantage that, in the regions in which the box-like ultrasonic transducer elements 6 rest on the damping layer 14, planar contact surfaces 15 can likewise be incorporated into the damping layer 14, so that when the intermediate product is fixed on the curved carrier 16, tensile stressing of the connection between the ultrasonic transducer element 6 and the conductor foil 2 at the edges of the ultrasonic transducer element 6 not lying in a common plane because of the curvature of the carrier 16, and the production of gaps as a result of separation of the ultrasonic transducer element 6 at these edges, are avoided.

Figure 4:
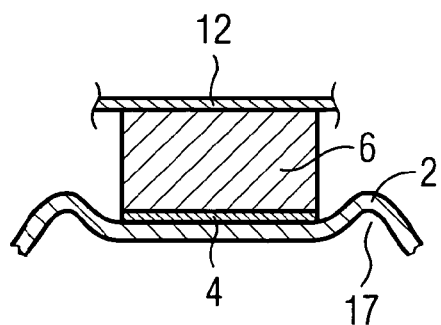
FIG. 4 is a sectional view of a detail likewise containing only one ultrasonic transducer element from the populated conductor foil configuration, in which the conductor foil configuration is provided with a fold beside the ultrasonic transducers.

As an alternative to this, the damping layer 14 can also be produced by pouring into a holder, which accommodates the conductor foil 2 populated with the ultrasonic transducer elements 6. In order in this case to ensure flat attachment of the ultrasonic transducer elements 6 to the carrier 16, according to FIG. 4 the conductor foil 2 between the ultrasonic transducer elements 6 is provided with a fold 17.

The absorber material 10 and the grounding foil 12 can be introduced or applied to the carrier 16 before or after the application of the conductor foil 2 provided with the damping layer 14 and populated with the ultrasonic transducer elements 6.

Figure 5:
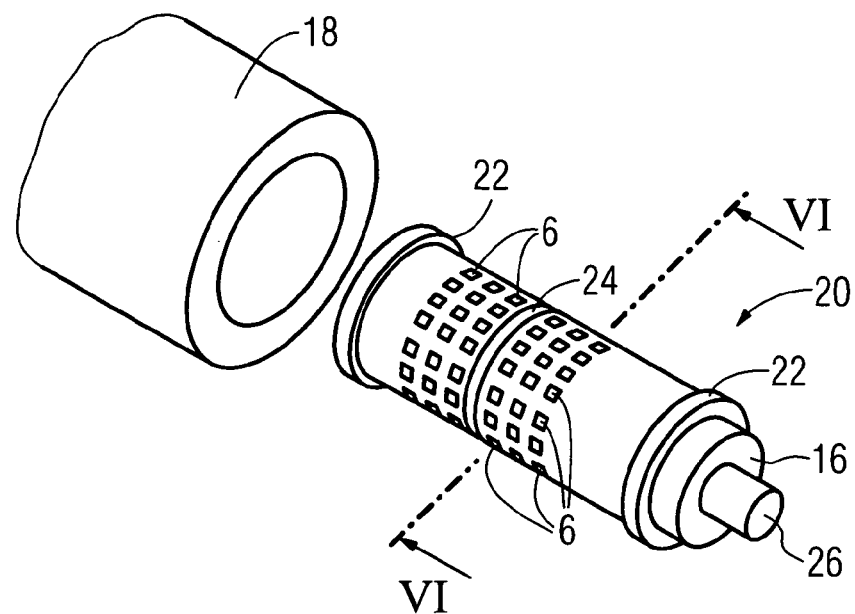
FIG. 5 is a perspective view of the test head suitable for testing a borehole.

According to FIG. 5, the intermediate product illustrated in FIG. 2 is applied to the carrier 16 matched to the surface contour or form of the workpiece 18 to be tested. In the example illustrated, the carrier 16 is cylindrical, so that it can be introduced into the interior of a pipe or workpiece 18 provided with a bore. The cylindrical test head 20 formed in this way, matched to the inner surface of the pipe or the bore—in the present case the inner wall of the pipe or of the bore—is provided at the mutually opposite ends thereof with annular sealing lips 22 which, in the inserted state, provide a defined coupling gap between the transmitting surfaces of the ultrasonic transducer elements 6 and the inner wall of the pipe or the bore, which gap can be filled with a coupling fluid, for example an oil. In the example of the figure, in addition to the ultrasonic transducer elements 6 arranged in the form of a matrix, an annular ultrasonic transducer 24 is arranged. The designation 26 indicates a socket or plug for the connection of signal cables, not shown in the figure.

Figure 6:
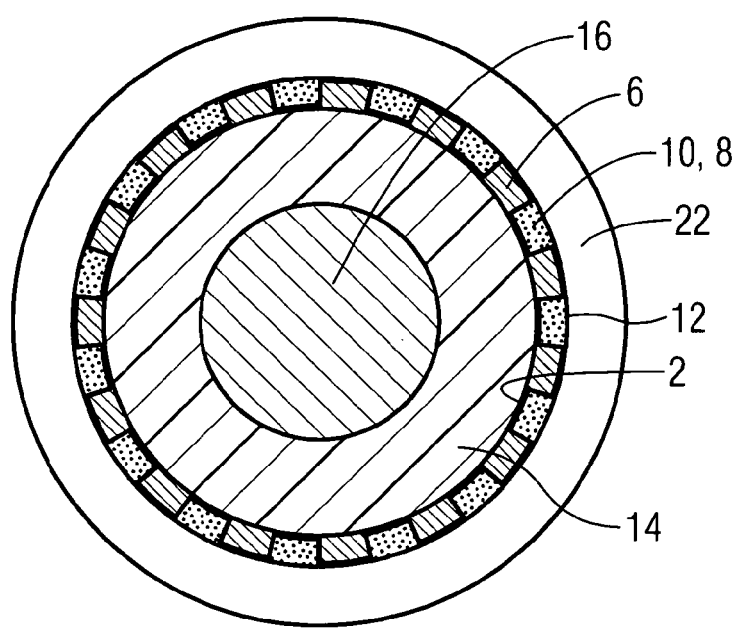
FIG. 6 is a cross-sectional view of the test head according to FIG. 3.

FIG. 6 shows the test head in a cross section, in which the conductor foil 2 and the grounding foil 12 are reproduced only roughly schematically. It can be seen clearly that the conductor foil 2 populated with the ultrasonic transducer elements 6 is arranged with the damping layer 14 on the cylindrical carrier 16. The interspaces 8 located between the ultrasonic transducer elements 6 are filled with the absorber material 10 and, jointly with the ultrasonic transducer elements 6, are covered with the grounding foil 12.

FIGS. 5 and 6 show a test head with which the entire circumference of the inner wall of the pipe 18 can be tested in a single axial test run. As an alternative to this, a test head can also contain a conductor foil provided with ultrasonic transducers with which only a segment of the inner wall, for example 120°, can be registered, so that, a plurality of axial test scans are necessary, for this example, four test scans.

If, on account of the physical testing conditions, the dimensions of the ultrasonic transducer elements 6 have to be chosen to be so small that effective signal transmission and signal reception is not possible because of the low capacitance in the transmitting and receiving circuit, piezoelectric stacks, as they are known, can also be used as ultrasonic transducers. Such a piezoelectric stack is illustrated in more detail in the exemplary embodiment according to FIG. 7. According to this exemplary embodiment, the ultrasonic transducer element 6 is built up from a plurality of piezoelectric elements 60 arranged one on another in the form of a stack. The piezoelectric stack formed in this way is arranged between the conductor foil 2 and the grounding foil 12. The piezoelectric elements 60 have a polarization, illustrated by arrows 62, with an orientation alternating between adjacent piezoelectric elements 60. Between the adjacent piezoelectric elements 60 there is an electrode 64, mutually adjacent electrodes 64 being connected to different terminals of a voltage source 66. In this way, the piezoelectric elements 60 are connected in parallel and the polarity of the voltage with which piezoelectric elements 60 following one another in the piezoelectric stack are excited alternates. Since the polarization likewise alternates, all the simultaneously excited piezoelectric elements 60 in the piezoelectric stack oscillate in the same phase, so that the amplitude of the ultrasonic pulses emitted by the piezoelectric stack increases with an increasing number of the piezoelectric elements, and high and short ultrasonic pulses can even be generated with small transmitting/receiving surfaces of the ultrasonic transducer.

Since all the piezoelectric elements are activated simultaneously by the same voltage source 66, the wiring in the piezoelectric stack is simplified. As a result of the lower thickness and therefore higher capacitance of the individual piezoelectric elements 60, as compared with an ultrasonic transducer built up from a single piezoelectric element which has the same dimensions as the piezoelectric stack, and also in addition as a result of the parallel connection thereof, the electrical impedance of the ultrasonic transducer 6 is reduced considerably. Since the electrical impedance of an ultrasonic transducer is proportional to the transmitting/receiving surfaces, in small ultrasonic transducers such as are needed in the test head according to the invention, the impedance can assume values which are considerably higher than the input impedance of 50 Ohm normally used in ultrasonic transducers and matched to the impedance of the feed lines used. As a result of the use of piezoelectric stacks and the associated increase in the capacitance, the impedance of the ultrasonic transducer and, accordingly, also the matching losses during the signal transmission can be reduced.

The invention claimed is:

1. A test head for testing a workpiece, the test head comprising:
    an ultrasonic transducer configuration having a plurality of ultrasonic transducers;
    a carrier matched to a surface contour of the workpiece;
    a damping layer disposed on said carrier; and
    a flexible conductor foil configuration disposed on said damping layer and having a number of electrically separated conductor lines corresponding to a number of said ultrasonic transducers, said ultrasonic transducers disposed on said conductor lines and disposed beside one another in at least one row and each of said ultrasonic transducers making electrical contact respectively with one of said conductor lines;

said damping layer and said flexible conductor foil configuration disposed between said ultrasonic transducer configuration and said carrier.

2. The test head according to claim 1, further comprising a coherent grounding foil disposed on said ultrasonic transducers on a side of said ultrasonic transducers facing away from said carrier.

3. The test head according to claim 1, further comprising an absorber material, said ultrasonic transducers are spaced apart from one another by interspaces, which are filled with said absorber material.

4. The test head according to claim 1, wherein said flexible conductor foil configuration includes a coherent conductor foil.

5. The test head according to claim 1, wherein said ultrasonic transducers are disposed beside one another in a plurality of rows.

6. The test head according to claim 1, wherein each of said ultrasonic transducers is built up from a plurality of piezoelectric elements disposed one on another in a form of a stack, between said piezoelectric elements an electrode is disposed in each case.

7. The test head according to claim 6, wherein said piezoelectric elements are connected in parallel.

8. The test head according to claim 7, wherein a polarization of each of said piezoelectric elements alternates, so that respectively adjacent ones of said piezoelectric elements have mutually opposed polarization.

9. A process for producing a test head, which comprises the steps of:

providing a conductor foil configuration having electrically mutually separated conductor tracks and a plurality of ultrasonic transducers, a contact-connection being made between the plurality of ultrasonic transducers and the conductor tracks;

applying a damping layer, which is flexible, at least during a processing time, to a reverse side of the conductor foil configuration facing away from the ultrasonic transducers; and applying the conductor foil configuration with the ultrasonic transducers and the damping layer to a carrier matched to a surface contour of a workpiece to be tested such that the conductor tracks and the damping layer are between the plurality of ultrasonic transducers and the carrier.

10. The process according to claim 9, which further comprises applying a coherent grounding foil to a side of the ultrasonic transducers facing away from the carrier.

11. The process according to claim 9, which further comprises:

disposing the ultrasonic transducers on the conductor foil configuration so as to be spaced apart from one another by interspaces; and filling the interspaces with an absorber material.

12. A process for producing a test head, which comprises the steps of:

providing a conductor foil configuration having electrically mutually separated conductor lines and a plurality of ultrasonic transducers, a contact-connection being formed between the plurality of ultrasonic transducers and the conductor lines;

applying the conductor foil configuration populated with the ultrasonic transducers to a pre-formed damping layer, which is flexible, at least during a processing time; and applying the conductor foil configuration having the ultrasonic transducers and the damping layer to a carrier matched to a surface contour of a workpiece to be tested such that the conductor lines and the damping layer are between the plurality of ultrasonic transducers and the carrier.

13. The process according to claim 12, which further comprises applying a coherent grounding foil to a side of the ultrasonic transducers facing away from the carrier.

14. The process according to claim 12, which further comprises:

disposing the ultrasonic transducers on the conductor foil configuration so as to be spaced apart from one another by interspaces; and filling the interspaces.

* * * * *